United States Patent
Kim et al.

(10) Patent No.: US 6,830,376 B2
(45) Date of Patent: Dec. 14, 2004

(54) RADIOACTIVE IMAGE APPARATUS AND FOCUS CONTROL METHOD THEREOF

(75) Inventors: Jae-Wan Kim, Suwon (KR); Jae-Hyun Jung, Anyang (KR); Hyeong-Cheol Kim, Seongnam (KR); Jun-Bo Kim, Seoul (KR); Won Choi, Suwon (KR); Hyoung-Jo Jeon, Yongin (KR)

(73) Assignee: Samsung Electronic Co., Ltd., Suwon-Si (KR)

( * ) Notice: Subject to any disclaimer, the term of this patent is extended or adjusted under 35 U.S.C. 154(b) by 256 days.

(21) Appl. No.: 10/282,070

(22) Filed: Oct. 29, 2002

(65) Prior Publication Data

US 2003/0223550 A1 Dec. 4, 2003

(30) Foreign Application Priority Data

Jun. 3, 2002 (KR) ........................................ 2002-31108

(51) Int. Cl.[7] .............................................. G01D 18/00
(52) U.S. Cl. ........................ 378/207; 378/205; 378/208
(58) Field of Search ................................ 378/207, 205, 378/163, 98.8, 208; 250/208.1; 382/255, 286

(56) References Cited

U.S. PATENT DOCUMENTS

| | | | | |
|---|---|---|---|---|
| 4,649,561 A | * | 3/1987 | Arnold | 378/207 |
| 5,818,064 A | | 10/1998 | Kohgami et al. | |
| 6,490,368 B2 | * | 12/2002 | Roder | 382/147 |
| 6,694,047 B1 | * | 2/2004 | Farrokhnia et al. | 382/132 |
| 2002/0080913 A1 | * | 6/2002 | Roder | 378/22 |

* cited by examiner

Primary Examiner—David V. Bruce
Assistant Examiner—Irakli Kiknadze
(74) Attorney, Agent, or Firm—Staas & Halsey LLP

(57) ABSTRACT

A radioactive image apparatus and a method of controlling a focus thereof. The radioactive image apparatus includes a radioactive ray generating unit, a robot table, and a radioactive ray detecting unit. The focus control method includes obtaining a radioactive transmission image of a test pattern, defining a circle with a given radius in the radioactive transmission image of the test pattern, detecting values of pixels located on a circumference of the circle, calculating the standard deviation of the values of the pixels located on the circumference of the circle, and determining the radius of the circle to be an index factor of a resolution in response to the calculated standard deviation being smaller than a preset threshold value.

31 Claims, 11 Drawing Sheets

RADIOACTIVE IMAGE APPARATUS AND FOCUS CONTROL METHOD THEREOF

CROSS-REFERENCE TO RELATED APPLICATIONS

This application claims the benefit of Korean Patent Application No. 2002-31108 filed on Jun. 3, 2002, in the Korean Industrial Property Office, the disclosure of which is incorporated herein by reference.

BACKGROUND OF THE INVENTION

1. Field of the Invention

The present invention relates to a radioactive image apparatus, and more particularly, to a radioactive image apparatus which uses radioactive rays to obtain an image of a subject and a method of controlling the focus thereof.

2. Description of the Related Art

Generally, radioactive image apparatuses are used in the medical field to detect abnormal conditions in a human body, and in an industrial field to determine the states of products. In the industrial field, for example, theses apparatuses are used to determine the internal states of the products where it is difficult to disassemble or check whether the products are defective.

FIG. 1 shows a conventional radioactive image apparatus which is used to test products in an industrial field. As shown in FIG. 1, when radioactive rays are irradiated from a radioactive ray generating unit 102 provided above a robot table 104, the radioactive rays pass through a star test pattern 106 mounted on the robot table 104 such that a transmission image 110 of the star test pattern 106 is formed on a radioactive ray detecting unit 108. The star test pattern 106 shown in FIG. 1 is a tool used to measure a focus of the radioactive ray generating unit 102. The star test pattern 106 is a radial arrangement of lead spoke patterns whose thickness becomes thinner toward the center of the radial arrangement.

FIGS. 2A and 2B show transmission images of test patterns obtained by the conventional radioactive image apparatus, in which FIG. 2A shows a satisfactory focus and FIG. 2B shows a dissatisfactory focus. That is, in FIG. 2A, lead spoke patterns are clearly shown in the vicinity of a center of a transmission image. In contrast, in FIG. 2B, lead spoke patterns are not clearly shown in the vicinity of a center of a transmission image.

If the focus is dissatisfactory, it is difficult to obtain a high resolution, and accordingly, the focus must be controlled again. FIG. 3 illustrates a conventional method of controlling a focus of the radioactive image apparatus shown in FIG. 1. First, a star test pattern 106 is mounted on a robot table 104 in operation 302, and a radioactive transmission image 110 is obtained by irradiating radioactive rays onto the star test pattern 106 in operation 304. Next, it is determined, with a naked eye, whether the focus of the radioactive transmission image 110 is satisfactory in operation 306. Where the focus is dissatisfactory, focus-related parameters are corrected in operation 310, and the operation 304 of obtaining the radioactive transmission image is performed again. If a subject has been mounted on the robot table 104, it is removed so as to re-mount the star test pattern 106 for the focus control.

Conditions for determining the resolution of the radioactive image apparatus include the magnitude of the focus of a radioactive source and the focus of an image pickup device which obtains a transmission image. The magnitude of the focus of the radioactive source is dependent on voltages, currents, etc., where an X ray tube is used as the radioactive source. The voltages and the currents should be adjusted frequently depending on the values of matter properties of the subject. In addition, the focus of the image pickup device can be varied by various factors. If some conditions such as the focus of the radioactive source and the focus of the image pickup device are changed, the focus should be controlled again to obtain an optimal resolution. However, in the prior art, naked eyes of the users were used to determine whether the focus was satisfactory. Accordingly, differences among the individuals determining whether the focus was satisfactory were significant, and controlling the focus again required a long period of time.

SUMMARY OF THE INVENTION

Accordingly, it is an object of the present invention to provide a radioactive image apparatus having a robot table provided with a jig equipped with various kinds of test patterns, wherein a position of the robot table is adjustable so as to obtain radioactive transmission images of the test patterns. Therefore, the present radioactive image apparatus allows appropriate test patterns to be conveniently used where the focus of the radioactive image apparatus is controlled.

Another object of the present invention is to provide a method of controlling a focus of a radioactive image apparatus, in which a determination of whether the focus is satisfactory is based on a comparison between deviations of pixel values of radioactive transmission images of test patterns and an adjustment of resolution-related parameters. The determination and adjustment operations are automatically performed in association with a computer of the radioactive image apparatus. Accordingly, the focus of the radioactive image apparatus is controlled with a very high accuracy as compared to a conventional focus control performed by a naked eye.

Additional objects and advantages of the invention will be set forth in part in the description which follows and, in part, will be obvious from the description, or may be learned by practice of the invention.

To achieve the above and other objects of the present invention, there is provided a radioactive image apparatus comprising a radioactive ray generating unit which irradiates radioactive rays onto a subject, an adjustable robot table having a subject fixing member which holds the subject, and a test pattern mounting member, wherein a position of the adjustable robot table is changeable to have the radioactive rays irradiated onto the subject, and a radioactive ray detecting unit which produces a radioactive transmission image formed by irradiating the radioactive rays onto the subject.

To achieve the above and other objects of the present invention, there is also provided a method of controlling a focus of a radioactive image apparatus having a radioactive ray generating unit which generates radioactive rays onto a subject, an adjustable robot table which includes a subject fixing member for positioning the subject and a test pattern mounting member for receiving one or more test patterns, and a radioactive ray detecting unit which produces a radioactive transmission image formed by irradiating the radioactive rays onto the subject, the method comprising obtaining a radioactive transmission image of the test pattern, defining a circle with a given radius in the radioactive transmission image of the test pattern, detecting values of pixels located on a circumference of the circle, calculating a standard deviation of the values of the pixels located on the circumference of the circle, and determining the radius of the circle to be an index factor of a resolution in response to the standard deviation being smaller than a preset threshold value.

BRIEF DESCRIPTION OF THE DRAWINGS

These and other objects and advantages of the present invention will become apparent and more readily appreciated from the following description of the embodiments, taken in conjunction with the accompanying drawings of which.

DETAILED DESCRIPTION OF THE PREFERRED EMBODIMENTS

Figure 1:
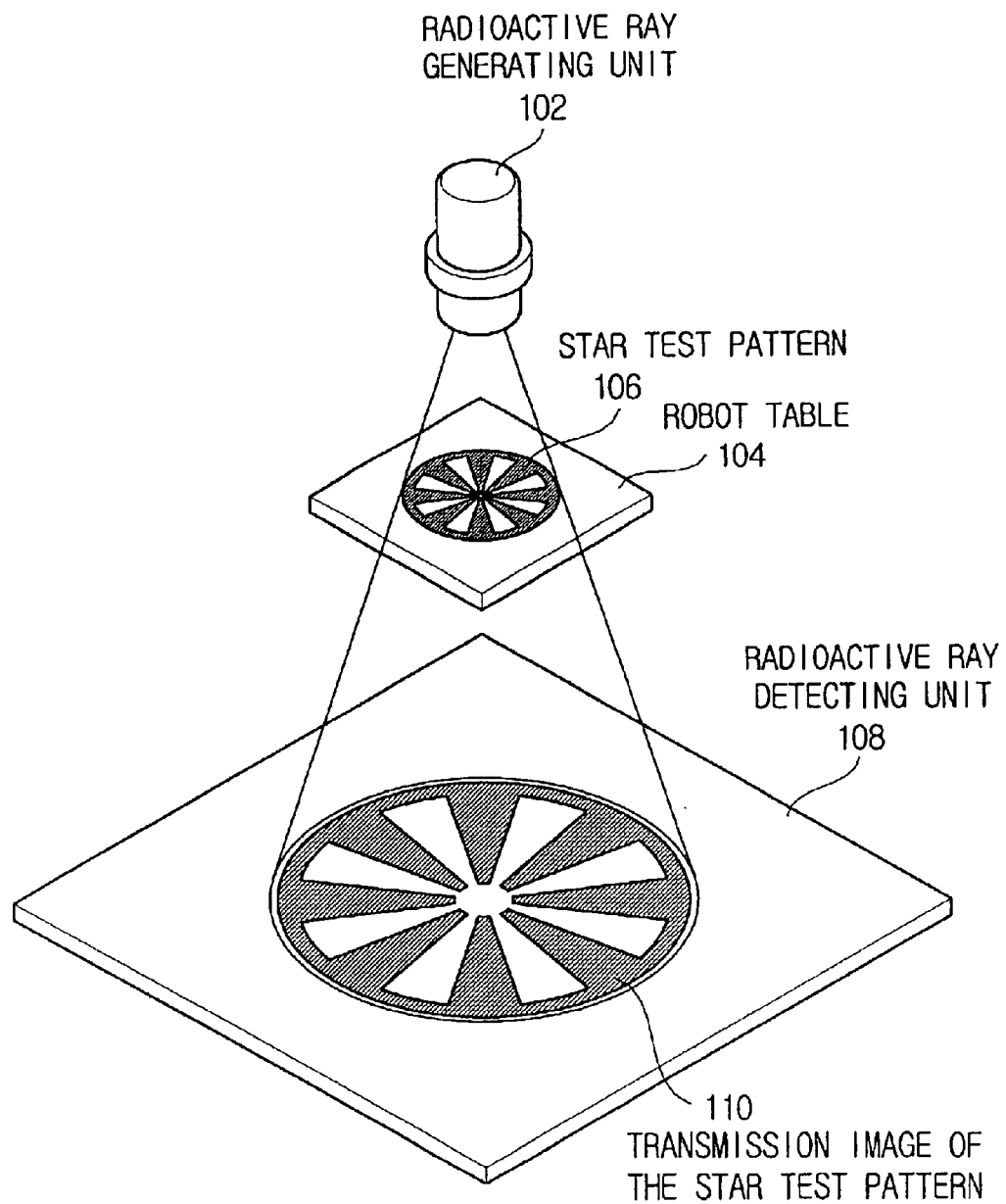
FIG. 1 is a diagram showing a conventional radioactive image apparatus.
Figure 2A:
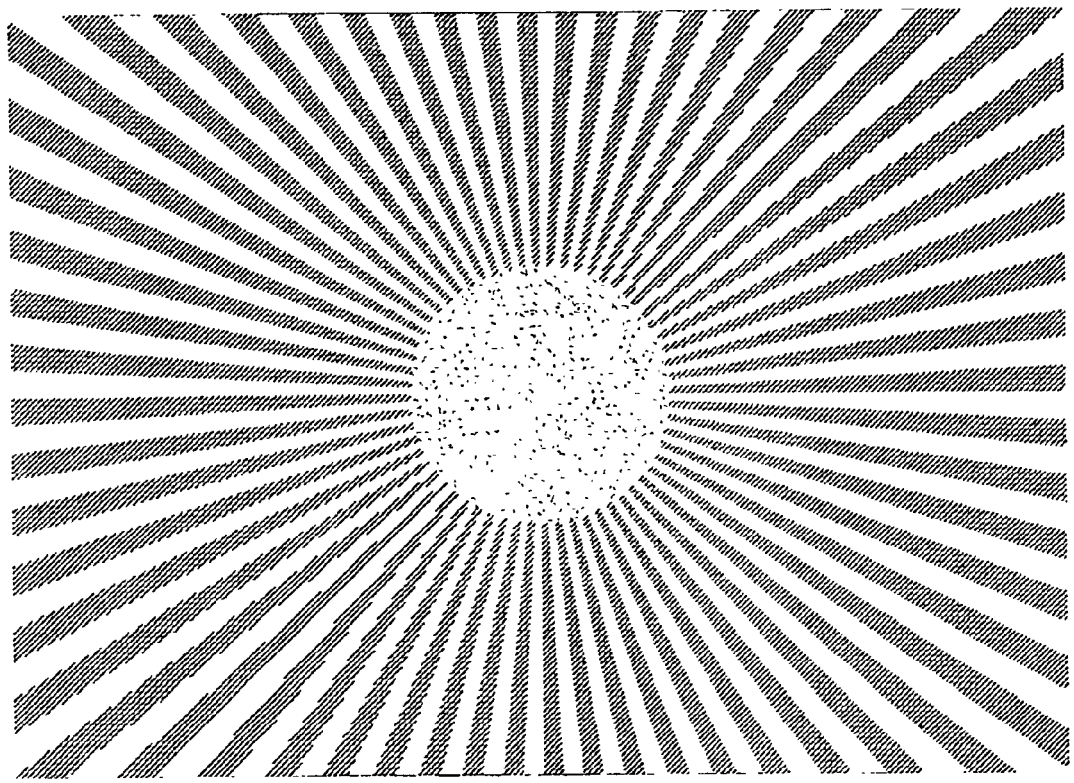
FIGS. 2A and 2B are transmission images of test patterns obtained by the conventional radioactive image apparatus shown in FIG. 1.
Figure 2B:
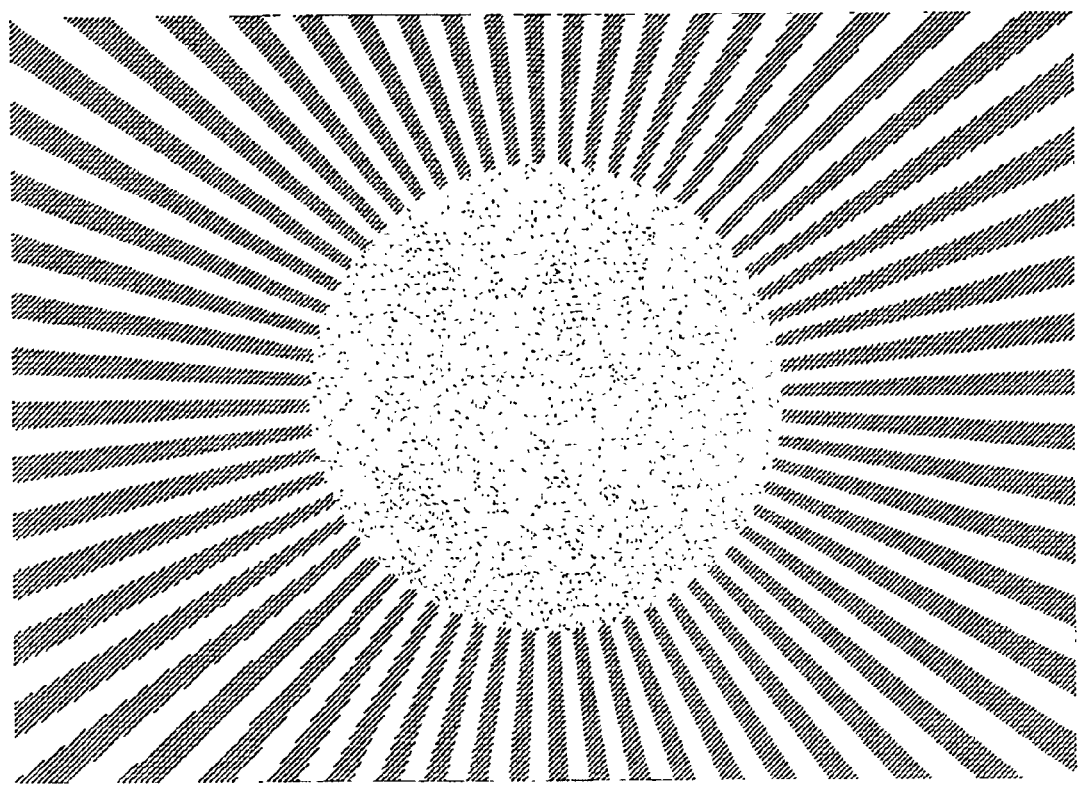
Figure 3:
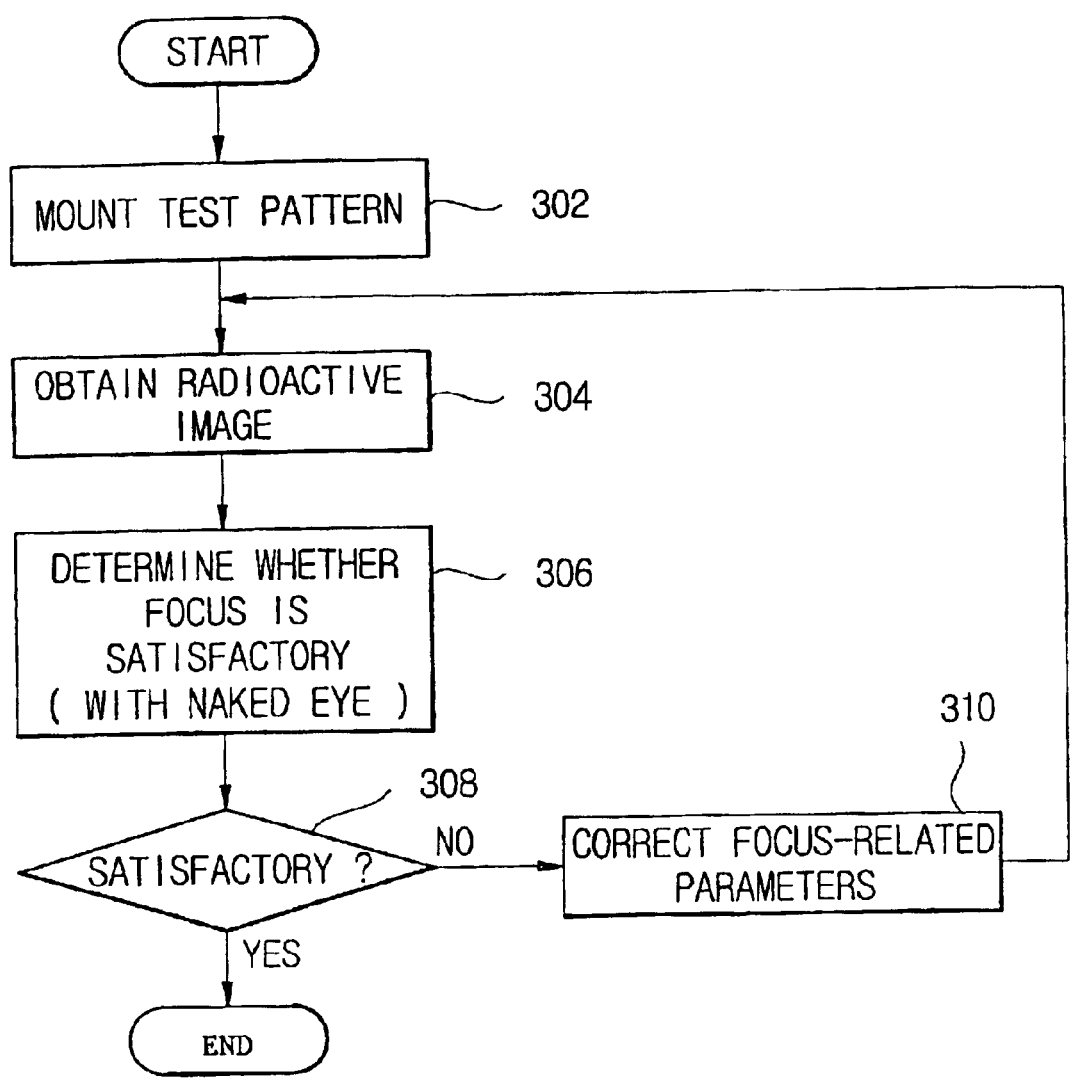
FIG. 3 is a flowchart explaining a method of controlling a focus of the radioactive image apparatus shown in FIG. 1.

Reference will now be made in detail to the embodiments of the present invention, examples of which are illustrated in the accompanying drawings, wherein like reference numerals refer to the like elements throughout. The embodiments are described below in order to explain the present invention by referring to the figures.

Figure 4:
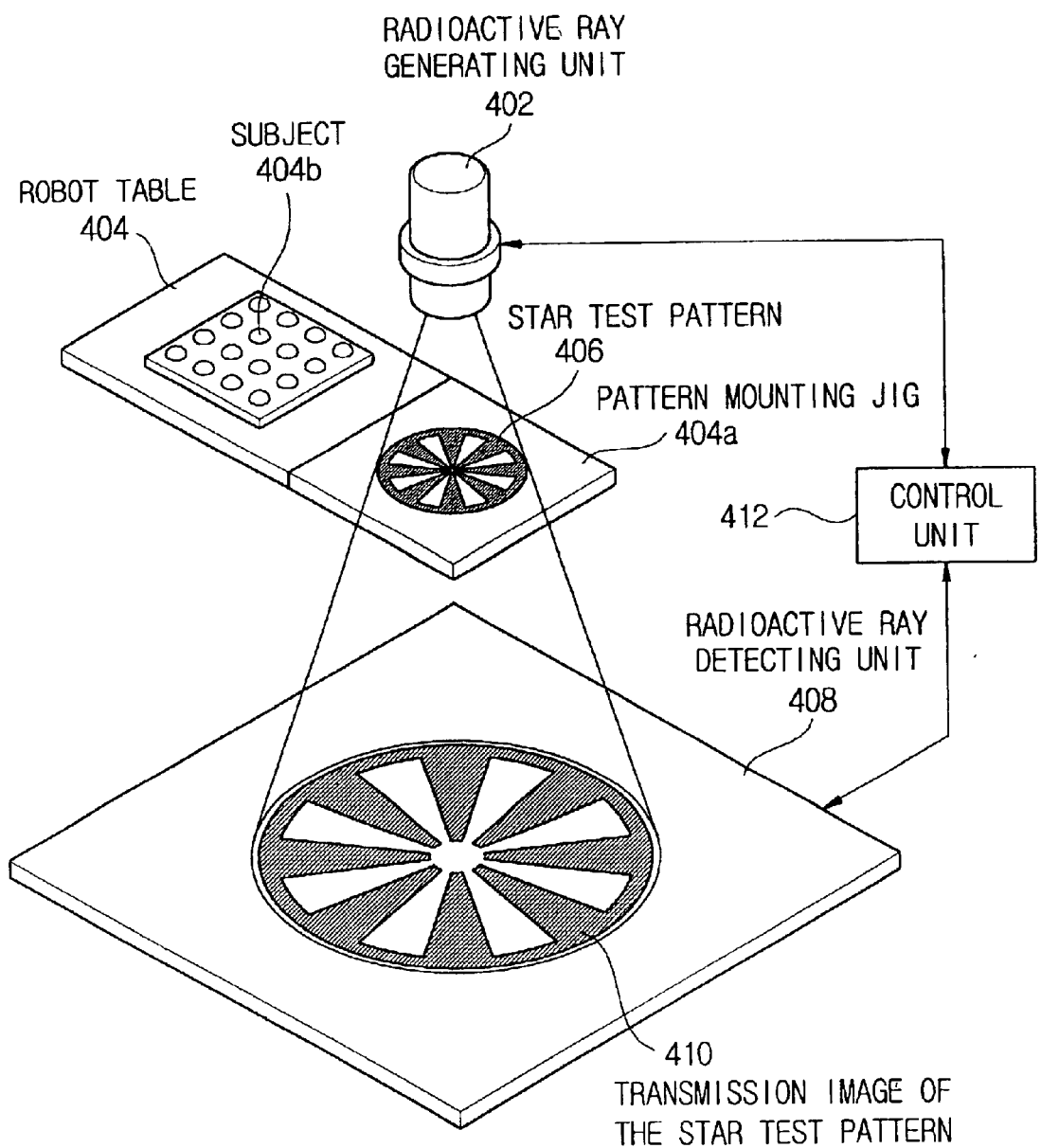
FIG. 4 is a diagram showing a configuration of a radioactive image apparatus according to an embodiment of the present invention.

FIG. 4 shows a configuration of a radioactive image apparatus in accordance with an embodiment of the present invention. As shown in FIG. 4, radioactive rays irradiated from a radioactive ray generating unit 402 provided above a robot table 404 pass through a star test pattern 406 mounted on the robot table 404 such that a transmission image 410 of the star test pattern 406 is formed in a radioactive ray detecting unit 408. When the radioactive ray detecting unit 408 and the radioactive ray generating unit 402 operate in association with a control unit 412, a detection of pixel values, a calculation of a standard deviation, etc., which are required to implement a focus control method of the present invention, are automatically performed. This enables a reduced focus control time and a precise focus control operation of the radioactive image apparatus.

A jig 404a which mounts the star test pattern 406 is attached to the robot table 404, on which a subject 404b is placed. Since more than one star test pattern 406 are mounted on the test pattern mounting jig 404a (see FIG. 5B), a position of the robot table 404 is adjusted at the time of focus control, so as to align the radioactive ray generating unit 402, the star test pattern 406 and the radioactive ray detecting unit 408. The radioactive rays are then irradiated on the star test pattern 406 to obtain the transmission image 410. Accordingly, where performance of another focus control is desired, focus control using a new test pattern can be conveniently performed by selecting another one of the various kinds of test patterns mounted on the test pattern mounting jig 404a, and adjusting the position of the robot table 404. In such a case, the position of the robot table 404 can be adjusted without a separate test pattern exchange. That is, since the focus control using the new test pattern can be performed only by adjusting the position of the robot table 404, the subject 404b on the robot table 404 need not be removed.

Figure 5A:
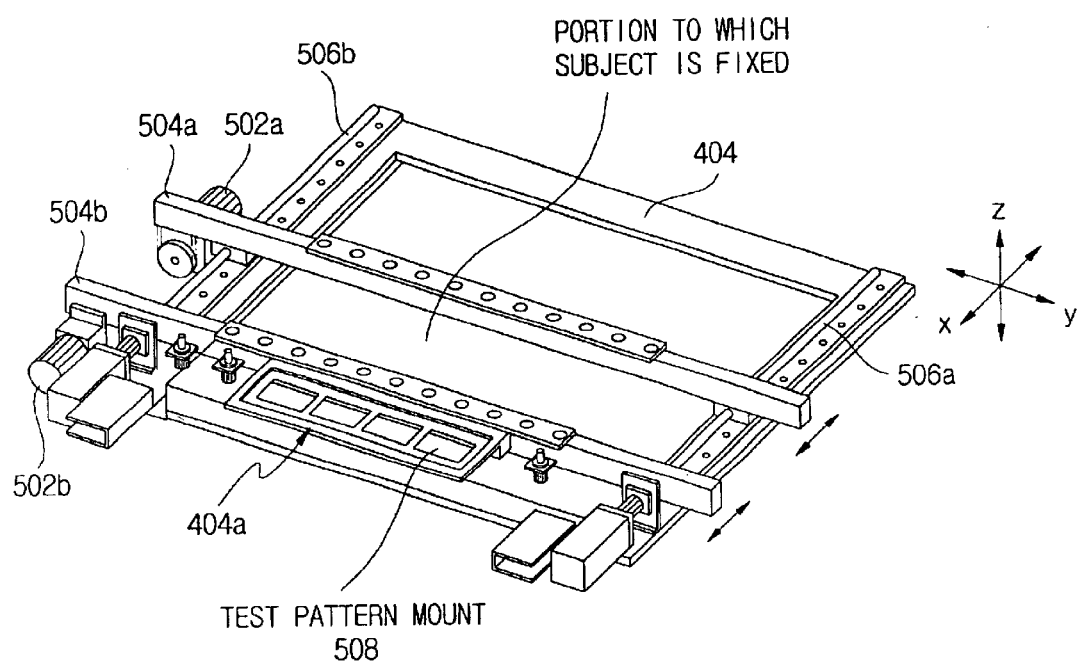
FIG. 5A is a diagram showing a robot table of the radioactive image apparatus shown in FIG. 4.

FIG. 5A shows the robot table 404 of the radioactive image apparatus of the present invention. The robot table 404 is operated by separate power equipment (not shown) to allow the robot table 404 to be moved three dimensionally. The robot table 404 has, for example, a square frame shape with an open center. The center portion is opened to obtain a pure transmission image of the subject where the radioactive rays are irradiated.

Guide rails 506a and 506b are formed parallel to each other at both ends of the square robot table 404. A pair of subject fixation members 504a and 504b are provided on the guide rails 506a and 506b, along which the pair of subject fixation members 504a and 504b can be moved in a straight line. The subject fixation members 504a and 504b actuated by motors 502a and 502b are moved along an X-axis, respectively. The subject (not shown) is inserted and fixed between the two subject fixation members 504a and 504b.

The test pattern mounting jig 404a is attached to an outer surface of the subject fixation member 504b. The test pattern mounting jig 404a is provided with several test pattern mounts 508 to allow various kinds of test patterns to be mounted thereon. Where the radioactive rays are irradiated while the subject fixation member 504b is moved, a desired pattern of radioactive transmission images can be easily obtained. In other words, by using the robot table 404 equipped with the test pattern mounting jig 404a of the present invention, the focus control can be conveniently performed using various kinds of test patterns without the need to exchange a test pattern for another test pattern.

Figure 5B:
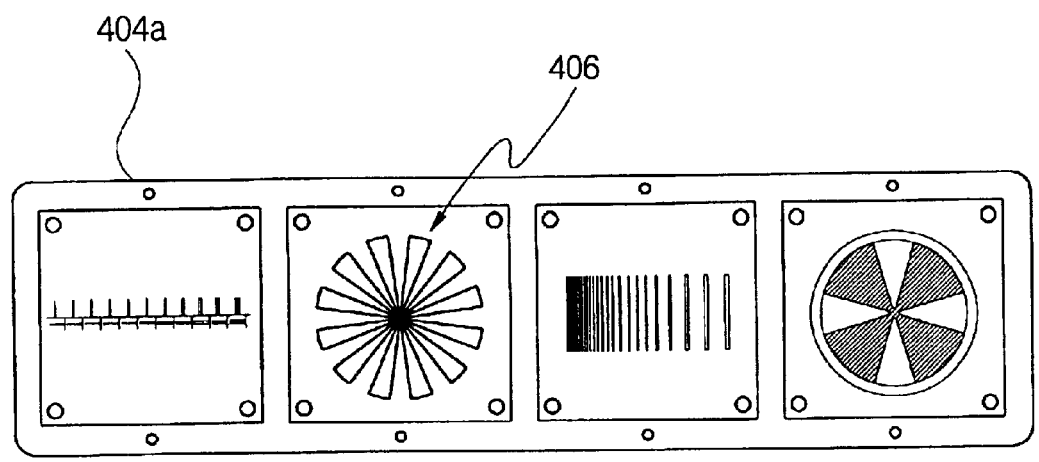
FIG. 5B is a diagram showing a test pattern mounting jig, which is provided on the robot table of the radioactive image apparatus shown in FIG. 4.

FIG. 5B shows the test pattern mounting jig 404a, which is provided on the robot table 404 of the radioactive image apparatus shown in FIG. 4. As shown in FIG. 5B, the test pattern mounting jig 404a is provided with a space in which various test patterns can be mounted. Accordingly, users can conveniently select a required pattern among the test patterns.

Figure 6:
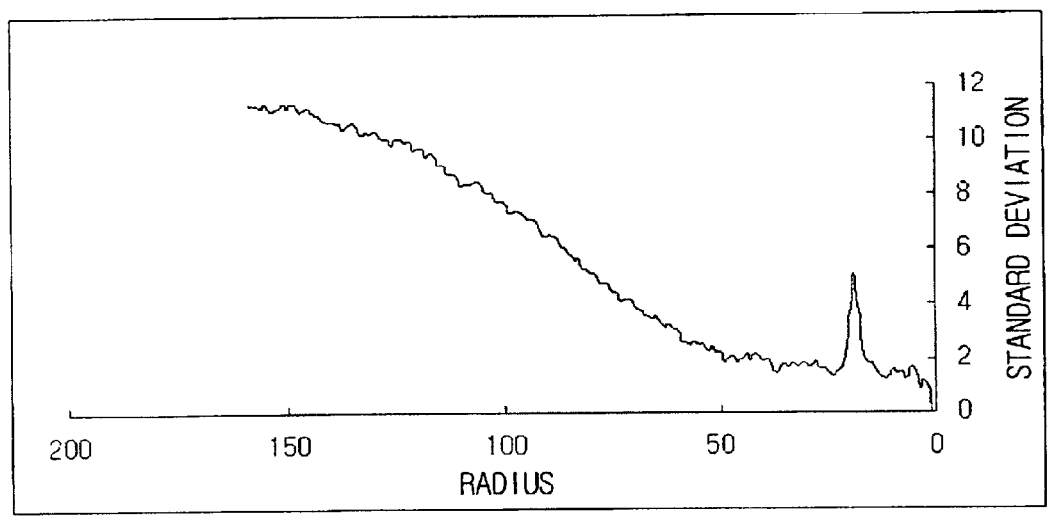
FIG. 6 is a graph illustrating a relationship between the radius of a circle, which indicates positions at which pixel values are detected, and the standard deviation of the values of the pixels located on the circumference of the circle, in a transmission image of a test pattern obtained by the radioactive image apparatus shown in FIG. 4.

FIG. 6 shows a graph illustrating a relationship between the radius of a circle, which indicates positions at which pixel values are detected, and the standard deviation of the values of the pixels located on the circumference of the circle, in a transmission image of a test pattern obtained by the radioactive image apparatus of the present invention. As shown in FIG. 6, the standard deviation of the values of the pixels located on the circumference of the circle is decreased as the radius of the circle is decreased. In other words, as it nears the center of the radioactive transmission image of the star test pattern, the clearness of lead spoke patterns is deteriorated such that the color of the background and the lead spoke patterns cannot be distinguished from each other with the standard deviation nearing zero. In contrast, as it moves away from the center of the transmission image, the color of the background and the lead spoke patterns become clearly distinguishable from each other with the standard deviation becoming relatively large.

Figure 7A:
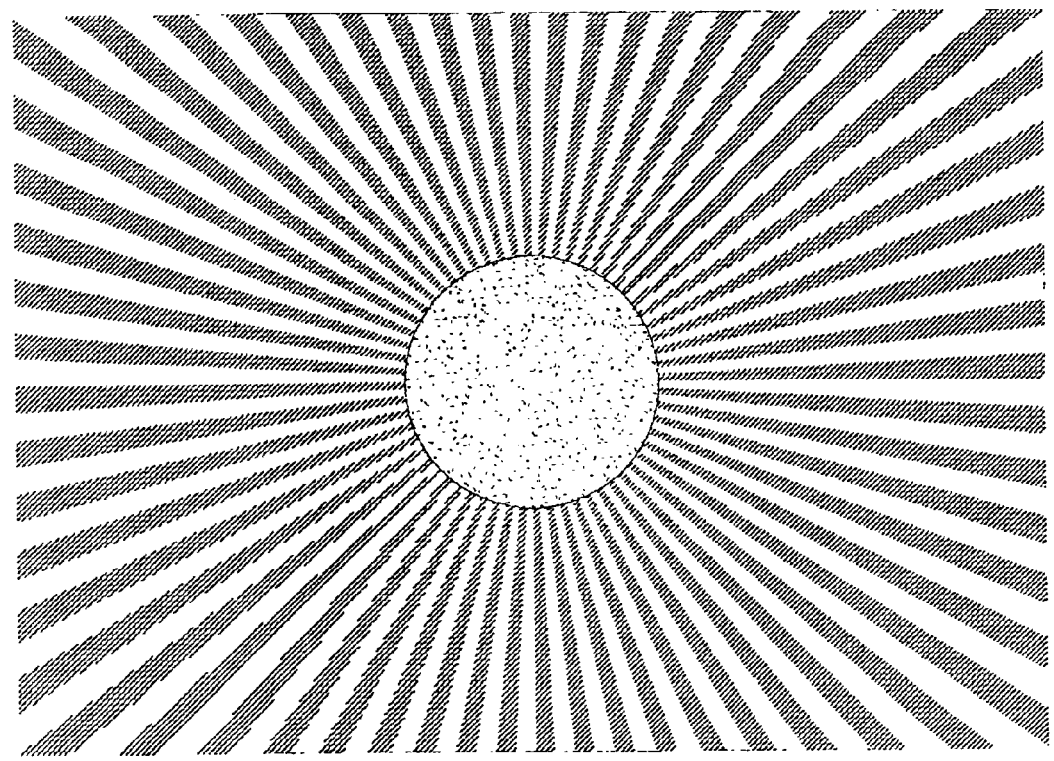
FIGS. 7A and 7B are diagrams showing transmission images of test patterns obtained by the radioactive image apparatus shown in FIG. 4.
Figure 7B:
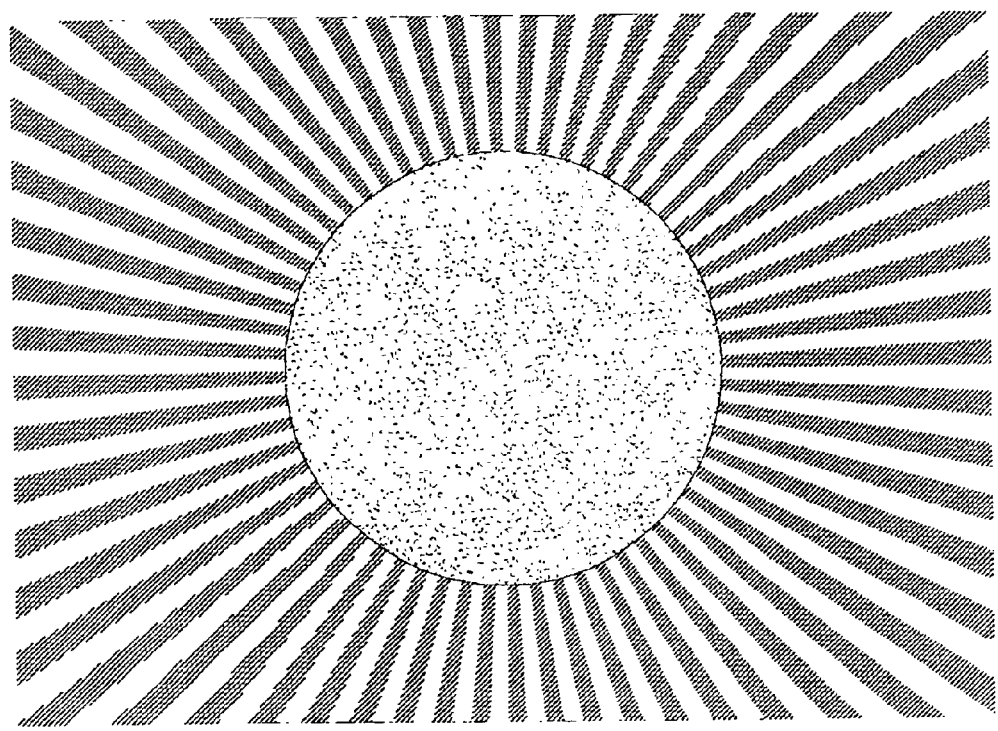

FIGS. 7A and 7B show images of test patterns obtained by the radioactive image apparatus of the present invention, in which FIG. 7A shows a satisfactory focus and FIG. 7B shows a dissatisfactory focus. That is, in FIG. 7A, the focus is satisfactory since the lead spoke patterns are relatively clear except a small portion around the center of the transmission image.

A circle in the center of the transmission image of FIG. 7A represents a position at which pixel values are sampled. A location at which the lead spoke patterns disappear from the transmission image can be determined by gradually reducing the radius of the circle until the standard deviation of the values of the pixels on the circumference of the circle reaches a preset threshold value. The location at which the lead spoke patterns disappear represents the magnitude of a resolution under current conditions.

In other words, since the smaller radius of the location at which the lead spoke patterns disappear means a higher resolution, a highest resolution image can be obtained by adjusting resolution-related parameters such that the radius of the location at which the lead spoke patterns disappear becomes minimal. More particularly, starting from initial values of the resolution-related parameters, the standard deviation of the pixel values is calculated while the position of the circle, i.e., the detection position of the pixel values, in the transmission images of the test patterns becomes gradually narrower.

Where the standard deviation reaches the preset threshold value, the radius of the circle is measured. While the resolution-related parameters are varied again at regular intervals, the radius of the circle is measured where the standard deviation reaches the preset threshold value. A value of the resolution-related parameter, at which the radius of the circle measured after the above described procedure is performed in a total range of the resolution-related parameters becomes minimal, is a value of the parameter at which the resolution becomes maximal under the current conditions. Accordingly, where the resolution-related parameter is adjusted to this value, a maximal resolution can be obtained.

A method of finding a location at which lead spoke patterns disappear according to the present invention includes a method of gradually decreasing a circle from a maximal size to a minimal size, and a method of gradually increasing the circle from the minimal size to the maximal size.

An embodiment of the focus control method of the radioactive image apparatus according to the present invention will be exemplified by the method of gradually decreasing the circle from the maximal size to the minimal size.

Figure 8:
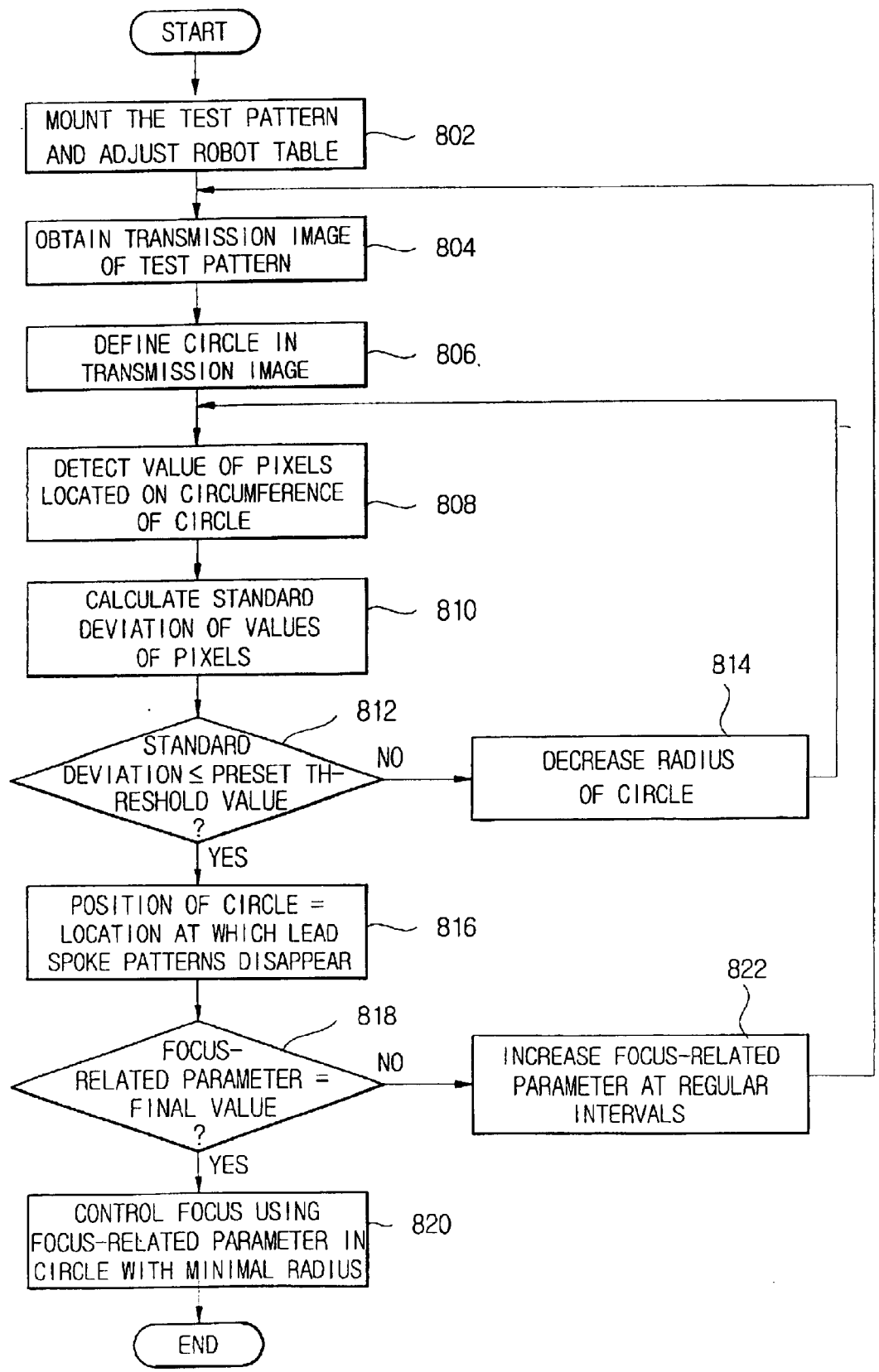
FIG. 8 is a flowchart illustrating a method of automatically controlling a focus of the radioactive image apparatus shown in FIG. 4.

FIG. 8, with reference to FIG. 4, illustrates a focus control method of the radioactive image apparatus of the present invention. First, the star test pattern 406 is mounted on the robot table 404, and the position of the robot table 404 is adjusted such that the radioactive rays pass through the star test pattern 406 in operation 802. Where the position adjustment of the robot table 404 is completed, a radioactive transmission image of the star test pattern 406 is obtained in operation 804.

Where a circle with a particular radius is defined in a center of a star test pattern in the transmission image, the values of the pixels located on the circumference of the circle are detected in operation 808. Where the values of pixels are detected, the standard deviation of the detected values of the pixels is calculated in operation 810 and compared to a preset threshold value in operation 812. The comparison of the calculated standard deviation and the threshold value is performed to determine whether a current position (or size) of the circle corresponds to a location at which lead spoke patterns of the transmission image disappear.

Where the standard deviation is larger than the threshold value, it is determined that the current position of the circle does not correspond to the location at which the lead spoke patterns of the transmission image disappear. This means that the radius of the circle needs to be decreased. Accordingly, where the standard deviation is larger than the threshold value, the radius of the circle is decreased in operation 814 to set a new size of circle, and the operation is returned to the operation of detecting the values of the pixels located on the circumference of circle. In contrast, where the standard deviation is smaller than the threshold value, it is determined that the current position of the circle corresponds to the location at which the lead spoke patterns of the transmission image disappear in operation 816. At the time, the focus nears to an optimal state as the radius of the circle becomes small.

Accordingly, where the radius of the circle is measured while the resolution-related parameters are increased at regular intervals throughout a total range of the resolution-related parameters, and the values of the resolution-related parameters of the radioactive image apparatus are adjusted by using focus-related parameters taken from a circle with a smallest radius among the measured circles, maximal resolution images can be obtained.

That is, where the radius of the circle becomes minimum in the operation 816, and a focus-related parameter of the circle is final, i.e., at a maximum, in operation 818, the focus is controlled using the focus-related parameter of the minimum radius circle in operation 820. Where the focus-related parameter of the circle is not final, the operation is returned to the operation of obtaining the image of the test pattern after increasing the focus-related parameter at regular intervals, i.e., gradually, in operation 822. For example, to obtain the minimum radius circle is to obtain a best focus, and to determine that the focus-related parameter is final is to obtain a best focus-related parameter in a preset range. Therefore, the best radioactive image can be obtained by increasing the focus-related parameter gradually, and controlling the focus using the focus-related parameter of the minimum radius circle.

In the focus control method of the radioactive image apparatus of the present invention, all of the detection of the values of the pixels located on the circumference, the calculation of the standard deviation, the comparison of the standard deviation and the threshold value, the comparison of the radius of the circle and a reference value, the determination of whether the focus is satisfactory, and the adjustment of the resolution-related parameters are automatically performed in association with a computer. Accordingly, a more precise determination of whether the focus is satisfactory can be made as compared to a conventional determination performed by a naked eye. In addition, since the resolution-related parameters are automatically adjusted such that a highest resolution is obtained, the time required for the focus control can be significantly reduced.

Furthermore, in the focus control method of the radioactive image apparatus of the present invention, the focus can be controlled by using various kinds of test patterns. While the focus is controlled by using the standard deviation of the values of the pixels located on the circumference, where a star test pattern is used, different types of figures including a circle can be used in the case where the focus is controlled by using different kinds of test patterns. In such a case, the determination of whether the focus is satisfactory can be made by using a distribution characteristic of values of pixels located on those figures.

As described above, the present invention provides a radioactive image apparatus having a test pattern mount which seats various kinds of test patterns, and a focus control method thereof, so as to easily perform the focus control. In addition, since whether the focus is satisfactory is determined by comparing the standard deviation of values of pixels with a threshold value through a computer, a time required for the focus control can be significantly reduced.

Although a few embodiments of the present invention have been shown and described, it will be appreciated by those skilled in the art that changes may be made in these embodiments without departing from the principles and spirit of the invention, the scope of which is defined in the appended claims and their equivalents.

What is claimed is:

1. A penetrating radiation image apparatus, comprising:
   a penetrating radiation generating unit which irradiates penetrating radiation onto a subject;
   an adjustable robot table which includes:
      a subject fixing member which holds the subject, and
      a test pattern mounting member, wherein a position of the adjustable robot table is changeable to have the penetrating radiation irradiated onto the subject; and
   a penetrating radiation detecting unit which produces a penetrating radiation transmission image formed by irradiating the penetrating radiation onto the subject.

2. The apparatus according to claim 1, wherein the test pattern member is fixed to the subject fixing member.

3. The apparatus according to claim 2, wherein:
   the subject fixing member comprises a pair of linearly movable units which station the subject, and
   the test pattern mounting member is mounted on one of the linearly movable units.

4. The apparatus according to claim 3, wherein a position of the test pattern mounting member is adjusted by moving the linearly movable units.

5. The apparatus according to claim 3, wherein the adjustable robot table further includes:
   guide rails along which the linearly movable units move; and
   one or more actuating motors which drive the linearly moveable units.

6. The apparatus according to claim 1, wherein the test pattern mounting member comprises a jig having pattern mounts for mounting one or more test patterns.

7. The apparatus according to claim 1, further comprising a control unit which defines a circle with a given radius in a produced penetrating radiation transmission image, calculates a standard deviation of values of pixels located on a circumference of the circle, and determines the radius of the circle to be an index factor of a resolution in response to the calculated standard deviation being smaller than a preset threshold value.

8. The apparatus according to claim 1, further comprising a control unit which defines a figure with a given feature in a produced penetrating radiation transmission image of the penetrating radiation image apparatus, calculates a standard deviation of values of pixels located on the figure and determines the feature of the figure to be an index factor of a resolution in response to the calculated standard deviation being smaller than a preset threshold value.

9. A method of controlling a focus of a penetrating radiation image apparatus having a penetrating radiation generating unit which generates penetrating radiation onto a subject, an adjustable robot table which includes a subject fixing member for positioning the subject and a test pattern mounting member for receiving one or more test patterns, and a penetrating radiation detecting unit which produces a penetrating radiation transmission image formed by irradiating the penetrating radiation onto the subject, the method comprising:
   obtaining a penetrating radiation transmission image of the test pattern;
   defining a circle with a given radius in the penetrating radiation transmission image of the test pattern;
   detecting values of pixels located on a circumference of the circle;
   calculating a standard deviation of the values of the pixels located on the circumference of the circle; and
   determining the radius of the circle to be an index factor of a resolution in response to the standard deviation being smaller than a preset threshold value.

10. The method according to claim 9, further comprising:
    varying the radius of the circle until the standard deviation becomes smaller than the preset threshold value in response to the standard deviation being larger than the preset threshold value; and
    determining the radius of the circle to be the index factor of the resolution in response to the standard deviation being smaller than the preset threshold value and the radius of the circle being smaller than a preset reference value.

11. The method according to claim 10, further comprising returning to the detecting of the values of the pixels located on the circumference of the circle after the varying of the radius of the circle in response to the standard deviation being larger than the preset threshold value.

12. The method according to claim 11, wherein the varying of the radius of the circle comprises one of gradually decreasing the radius of the circle and gradually increasing the radius of the circle.

13. The method according to claim 9, further comprising finding resolution-related parameters at which the radius of the circle is minimal in response to the standard deviation being smaller than the preset threshold value.

14. The method according to claim 13, further comprising returning to the obtaining of the image of the test pattern after adjusting the resolution-related parameters at regular intervals so as to find focus-related parameters for obtaining the resolution-related parameters at which the radius of the circle is minimal.

15. The method according to claim 14, further comprising controlling the focus using the focus-related parameters.

16. The method according to claim 14, further comprising obtaining a desired resolution of the penetrating radiation transmission image by adjusting values of the resolution-related parameters using the focus-related parameters.

17. The method according to claim 14, wherein the adjusting of the resolution-related parameters at the regular intervals is automatically performed in association with a control unit of the radioactive image apparatus.

18. The method according to claim 13, further comprising controlling the focus using the resolution-related parameters at which the radius of the circle is minimal.

19. The method according to claim 9, wherein the test pattern is a star test pattern in which lead spokes are formed radially and become thinner toward a center of the test pattern.

20. The apparatus according to claim 1, wherein the adjustable robot table is movable in three axes.

21. The apparatus according to claim 1, further comprising a control unit which controls a focus of a produced penetrating radiation transmission image of the radioactive image apparatus.

22. The apparatus according to claim 21, wherein the control unit determines whether the focus is satisfactory according to a distribution characteristic of values of pixels located on the produced penetrating radiation transmission image.

23. The apparatus according to claim 22, wherein the control unit adjusts resolution related parameters of the produced penetrating radiation transmission image in accordance with the distribution characteristic of the values of the pixels.

24. The method according to claim 9, wherein the detecting of the values of the pixels, calculating of the standard deviation and determining of the radius of the circle to be the index factor of the resolution are automatically performed in association with a control unit of the penetrating radiation image apparatus.

25. A method of controlling a focus of a penetrating radiation image apparatus having a penetrating radiation generating unit which generates penetrating radiation onto a subject, an adjustable robot table which includes a subject fixing member for positioning the subject and a test pattern mounting member for receiving one or more test patterns, and a penetrating radiation detecting unit which produces a penetrating radiation transmission image formed by irradiating the penetrating radiation onto the subject, the method comprising:

obtaining a penetrating radiation transmission image of the test pattern;

defining a figure with a given feature in the penetrating radiation transmission image of the test pattern;

detecting values of pixels located on the figure;

calculating a standard deviation of the values of the pixels located on the figure; and determining the feature of the figure to be an index factor of a resolution in response to the standard deviation being smaller than a preset threshold value.

26. The method according to claim 25, further comprising:

varying the feature of the figure until the standard deviation becomes smaller than the preset threshold value in response to the standard deviation being larger than the preset threshold value; and determining the feature of the figure to be the index factor of the resolution in response to the standard deviation being smaller than the preset threshold value and a value of the feature of the figure being smaller than a preset reference value.

27. The method according to claim 26, further comprising returning to the detecting of the values of the pixels located on the figure after the varying of the feature of the figure in response to the standard deviation being larger than the preset threshold value.

28. The method according to claim 25, further comprising finding resolution-related parameters at which the feature of the figure is minimal in response to the standard deviation being smaller than the preset threshold value.

29. The method according to claim 28, further comprising returning to the obtaining of the image of the test pattern after adjusting the resolution-related parameters at regular intervals so as to find focus-related parameters for obtaining the resolution-related parameters at which the feature of the figure is minimal.

30. The method according to claim 29, further comprising controlling the focus using the focus-related parameters.

31. The method according to claim 28, further comprising controlling the focus using the resolution-related parameters at which the feature of the figure is minimal.

* * * * *